United States Patent [19]

Timmons et al.

[11] Patent Number: 5,354,784
[45] Date of Patent: Oct. 11, 1994

[54] CYCLOPENTADIENYLIRON COMPLEX SALT, PROCESS FOR PREPARING THE SAME AND PHOTOPOLYMERIZABLE COMPOSITION CONTAINING THE SAME

[75] Inventors: Scott F. Timmons, San Antonio, Tex.; Hiroshi Sawada, Osaka, Japan; Stephen T. Willinghoff, San Antonio, Tex.; Robert E. Lyle, Jr., San Antonio, Tex.; Belinda K. Taylor, San Antonio, Tex.

[73] Assignee: Arakawa Kagaku Kogyo Kabushiki Kaisha, Osaka, Japan

[21] Appl. No.: 926,286

[22] Filed: Aug. 10, 1992

[51] Int. Cl.$^5$ ............... C08F 2/50; C08F 4/42; C07F 17/02
[52] U.S. Cl. ............... 522/33; 522/46; 522/66; 522/170; 522/181; 556/7; 556/13; 556/70; 556/87; 556/138
[58] Field of Search ............ 556/7, 13, 70, 140, 556/28, 30, 87, 138; 522/33, 46

[56] References Cited

U.S. PATENT DOCUMENTS

| | | | |
|---|---|---|---|
| 4,868,288 | 9/1989 | Meier | 566/140 |
| 5,059,701 | 10/1991 | Kiepert | 556/13 |
| 5,082,952 | 1/1992 | Meier | 556/7 |
| 5,089,536 | 2/1992 | Palazzotto | 556/7 |
| 5,110,964 | 5/1992 | Hiroi | 556/140 |

OTHER PUBLICATIONS

Schmidt et al. "Eine Effiziente Methode..." Journal of Organometallic Chem., 209 (1981). pp. 373–384.
Lee et al "Keto Complexes From..." Journal of Organometallic Chem., 207 (1984), pp. 157–170.
Lee et al "The Synthesis..." Journal of Organometallic Chem., 310 (1986). pp. 391–400.

Primary Examiner—Marion L. Mc Camish
Assistant Examiner—Arthur H. Koeckert
Attorney, Agent, or Firm—Varndell Legal Group

[57] ABSTRACT

A keto arene-cyclopentadienyl iron complex salt of the formula:

$$[(R^2CO)(R^1)_m C_6H_{5-m}Fe^{II}Cp]^{+1}A^{-1}$$

wherein $R^1$ is an alkyl group, $R^2$ is an alkyl group or phenyl group, m is an integer of 1 to 5, Cp is an $\eta^5$-cyclopentadienyl group and $A^{-1}$ is a non-nucleophilic anion, e.g. pentamethylacetophenone-Fe(II)-Cp$+$PF$_6$$^{-1}$ salt or pentamethylbenzophenone-Fe(II)-Cp$+$PF$_6$$^{-1}$ salt, which is useful as a photoinitiator for cationically polymerizable compounds, especially for epoxy resins, and has an improved environmental safety and a high absorptivity, and which can be easily produced by a direct replacement reaction between dicarbonyl-$\eta^5$-(2,4-cyclopentadien-1-yl)iron(II) halide and an alkyl substituted keto arene to be replaced for the carbonyl ligands.

6 Claims, 4 Drawing Sheets

CYCLOPENTADIENYLIRON COMPLEX SALT, PROCESS FOR PREPARING THE SAME AND PHOTOPOLYMERIZABLE COMPOSITION CONTAINING THE SAME

BACKGROUND OF THE INVENTION

The present invention relates to a cyclopentadienyliron complex salt, and more particularly to an ($\eta$-ketoarene)-($\eta$-cyclopentadienyl)iron(II) salt useful as a photoinitiator. The present invention also relates to a process for preparing the complex salt and a photopolymerizable composition containing it as a self sensitized initiator.

Since the first reported synthesis of a metal sandwich compound almost forty years ago [T. J. Keally and P. L. Pauson, Nature 1951, 168, 1039], there has been significant interest in the chemistry and properties of these transition metal complexes. Transition metal complexes of the type $(arene)_2M^{+n}$, where arene is a charged or uncharged aromatic species and $M^{+n}$ is a transition metal such as $Cr^{+2}$ or $Fe^{+2}$, are known to activate the arene(s) to nucleophilic substitution and increase the acidity of $\alpha$ alkyl protons. Mixed arene metal sandwiches of the type Cp-Fe(II)-arene, where Cp is deprotonated cyclopentadiene and the arene is a neutral aromatic compound such as mesitylene, have been extensively studied [D. Astruc, Tetrahedron 1983, 39(24), 4027].

There are two important methods for the production of Cp-Fe(II)-arene complexes. The first method involves exchanging the carbonyls in dicarbonyl-$\eta^5$-(2,4-cyclopentadien-1-yl)iron(II) halide for an arene under the influence of a Lewis acid such as aluminum chloride [T. H. Coffield, V. Sandel, R. D. Closson, J. Am. Chem. Soc., 1957, 79, 5826]. This method yields complexes in fair yield (40%) but suffers from the production of various side products lowering overall yield. By far the most useful method for the production of these compounds is to exchange the cyclopentadienyl ligand of ferrocene for the arene in the presence of aluminum chloride and aluminum dust [A. N. Nesmeyanov, N. A. Vol'kenau, E. L. Sirotkina and L. S. Shilovseva, Kokl. Akad. Nauk, SSSR 1965, 166, 607]. This second method has become the standard method for the production of these complexes since the starting material is readily available and yields are better.

For sandwich complexes of this type, the functionalization of the neutral aromatic compound has been rather limited. There are numerous examples of electron donor substituted aromatic exchange reactions and relatively few examples of exchange reactions involving electron acceptor substituted aromatic compounds [D. Astruc, Tetrahedron 1983, 39(24), 4027]. Some examples of electron acceptor substituted arenes include the halogenated aromatics and exocyclic heteroatom aromatics such as aniline. Although these examples are well known, the yields are generally low even under the most drastic conditions. For example, the degree of halogenation significantly influences the yield so that mono and dihalogenated arene complexes can be obtained but trihalogenated arene complexes are not known. In the case of exocyclic heteroatom aromatics, the conditions must be drastic and the yields are often low [J. F. Helling and W. A. Hendrickson, J. Organomet. Chem. 1979, 168, 87]. Electron acceptor groups on the arene inhibit or prevent ligand exchange. Additionally, the requirement of a rather strong Lewis acid to catalyze the ligand exchange limits the possible candidate aromatic ligand to one which is stable under these conditions. To date there has been no example of a direct exchange of a keto arene, perhaps as a result of the electron withdrawing nature of the conjugated carbonyl group or the formation of a complex with the aluminum chloride.

It is reported that chlorobenzene-Fe(II)-Cp is converted to acetophenone-Fe(II)-Cp via substitution of the chlorine on the arene with ethyl nitrite followed by a Nef type hydrolysis of the intermediate nitro species by hydrochloric acid (U. S. Gill, Inorg. Chem. Acta, 1986, 114, L25). However, yields for this reported reaction are highly variable and the optimal conditions are not known. A simpler method to produce a keto substituted arene complex is highly desirable.

European Patent No. 126,712 discloses that various arene metal sandwich complexes are useful as photoinitiators for cationic polymerization of monomers such as epoxides, representative examples of which are Cp-Fe(II)-arene wherein the arene is benzene, toluene, cumene, naphthalene, anthracene, phenanthrene or pyrene. This type of compound is photolyzed by near UV or visible radiation with release of arene to form a Cp-Fe(II) ion. It is important that the UV energy absorption of the arene complex at 365 nm is sufficient to initiate a polymerization. The absorptivity of the proposed Cp-Fe(II)-arene initiators increases with increasing the numbers of benzene rings. Anthracene-Fe(II)-Cp and pyrene-Fe(II)-Cp complex salts are usable as self sensitized initiators. However, these initiators may impair environmental safety due to release of harmful arene such as pyrene into the environment. The UV energy absorptivity of benzene-Fe(II)-Cp and cumene-Fe(II)-Cp is not sufficient initiate a polymerization at an acceptable speed. European Patent No. 126,718 proposes to use a cumene-Fe(II)-Cp initiator in the presence of a peroxide and an external sensitizer.

It is an object of the present invention to provide a novel (keto substituted $\eta^6$-arene)-($\eta^5$-cyclopentadienyl)iron(II) complex salt.

A further object of the present invention is to provide a (keto substituted $\eta^6$-arene)-($\eta^5$-cyclopentadienyl)iron(II) complex salt which is useful as a self sensitized photoinitiator for cationically polymerizable monomers, especially for epoxide compounds.

A still further object of the present invention is to provide a photoinitiating system which can initiate polymerization with a minimized release of arene during or after polymerization and which applicable to a polymerization system containing both a cationically polymerizable monomer and a radically polymerizable monomer without requiring any presence of a peroxide and a sensitizer.

Another object of the present invention is to provide a keto substituted arene complex as an intermediate to produce an epoxidized arene complex by a known method.

Still another object of the present invention is to provide a simple process for preparing a keto substituted arene metal complex by a direct replacement of a keto arene.

These and other objects of the present invention will become apparent from the description hereinafter.

SUMMARY OF THE INVENTION

It has been found that in a direct replacement of the carbonyls in dicarbonyl-$\eta^5$-(2,4-cyclopentadien-1-yl)iron(II) halide or the cyclopentadienyl ligand in ferrocene by an arene according to known methods, electron acceptor groups such as acyl group on the arene inhibit or prevent the ligand replacement because of withdrawing electron density from the ring, but that electron density can be compensated for by other electron donor groups such as alkyl groups and, therefore, keto arene transition metal complexes can be easily produced in fair yield by a direct replacement of keto arene when electron donor groups are present on the keto arene to be substituted.

In accordance with the present invention, there is provided a cyclopentadienyliron complex salt represented by the formula (1):

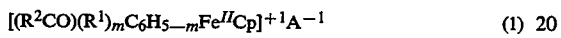

$$[(R^2CO)(R^1)_mC_6H_{5-m}Fe^{II}Cp]^{+1}A^{-1} \quad (1)$$

wherein $R^1$ is an alkyl group, m is an integer of 1 to 5, $R^2$ is an alkyl group or phenyl group, Cp is an $\eta^5$-cyclopentadienyl group and $A^{-1}$ is a non-nucleophilic anion.

The cyclopentadienyliron complex salt (1) can be prepared easily by a process which comprises:

(a) reacting a dicarbonyl-($\eta^5$-cyclopentadienyl)iron(II) halide with an acyl-alkyl-benzene represented by the formula (2):

$$R^2COC_6H_{5-m}R^1_m \quad (2)$$

wherein $R^1$, $R^2$ and m are as defined above, in the presence of a Lewis acid at an elevated temperature to produce a (keto-arene)-(cyclopentadienyl)iron complex represented by the formula (3):

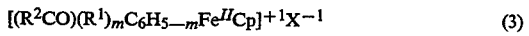

$$[(R^2CO)(R^1)_mC_6H_{5-m}Fe^{II}Cp]^{+1}X^{-1} \quad (3)$$

wherein $R^1$, $R^2$ and m are as defined above, Cp is a $\eta^5$-cyclopentadienyl group and X is a halogen atom, and (b) metathesizing the iron complex with an alkali metal salt of a non-nucleophilic acid.

The cyclopentadienyliron complex salts (1) are useful as a photoinitiator for cationically polymerizable monomers, particularly for epoxide monomers. Also, alkyl-substituted benzophenone-cyclopentadienyliron salts according to the present invention serve as a radical polymerization initiator and, therefore, they can also be utilized as a photoinitiator for a polymerization system containing a radically polymerizable monomer.

DETAILED DESCRIPTION

Figure 1:
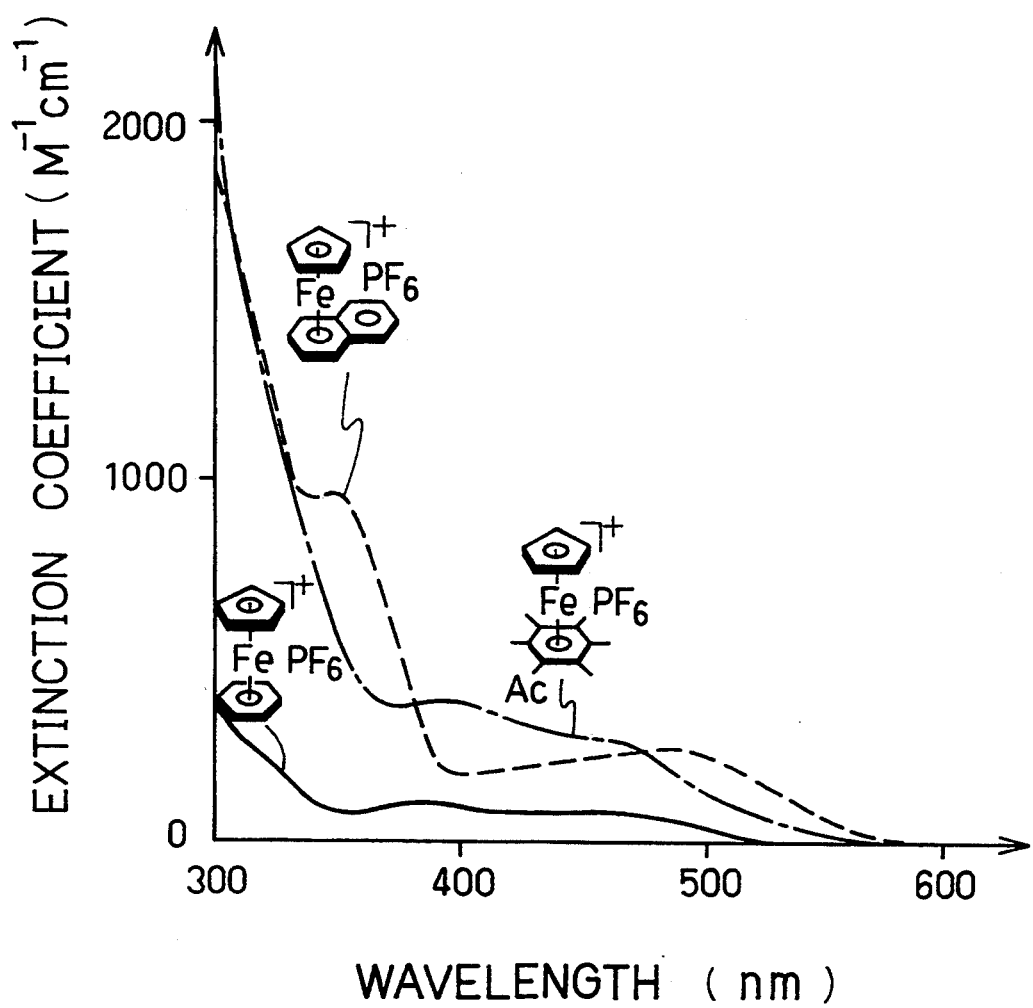
FIG. 1 is a plot of molar extinction coefficient vs. wavelength for (acetylpentamethyl-$\eta^6$-benzene)-($\eta^5$-cyclopentadienyl)iron(II) hexafluorophosphate according to the present invention, ($\eta^6$-naphthalene)-($\eta^5$-cyclopentadienyl)iron(II) hexafluorophosphate and ($\eta^6$-benzene)-($\eta^5$-cyclopentadienyl)iron(II) hexafluophosphate.

In the cyclopentadienyliron complex salt according to the invention, represented by the formula (1), $R^1$ is an alkyl group attached to the $\eta^6$-benzene ring, the carbon number of which is usually from 1 to 5, preferably from 1 to 3. The number of alkyl groups on the benzene ring is from 1 to 5, preferably 3 to 5, the most preferably 5.

In the acyl group $R^2CO$ attached to the benzene ring, $R^2$ is an alkyl group, especially an alkyl group having 1 to 5 carbon atoms, or phenyl group.

The non-nucleophilic anion $A^{-1}$ includes, for example, $BF_4^-$, $PF_6^-$, $AsF_6^-$, $SbF_6^-$, $FeCl_4^-$, $SnCl_5^-$, $SbCl_6^-$ and $BiCl_5^-$.

The cyclopentadienyliron complex salt of the present invention represented by the formula (1):

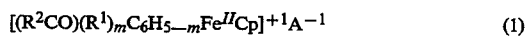

$$[(R^2CO)(R^1)_mC_6H_{5-m}Fe^{II}Cp]^{+1}A^{-1} \quad (1)$$

wherein $R^1$ is an alkyl group, m is an integer of 1 to 5, $R^2$ is an alkyl group or phenyl group, Cp is an $\eta$-cyclopentadienyl group and $A^{-1}$ is a non-nucleophilic anion, is easily prepared by a direct exchange reaction between dicarbonyl-$\eta^5$-(2,4-cyclopentadien-1-yl)iron(II) halide and alkyl-substituted keto arene according to a known manner, followed by metathesis with a suitable anion such as $PF_6$, as shown below.

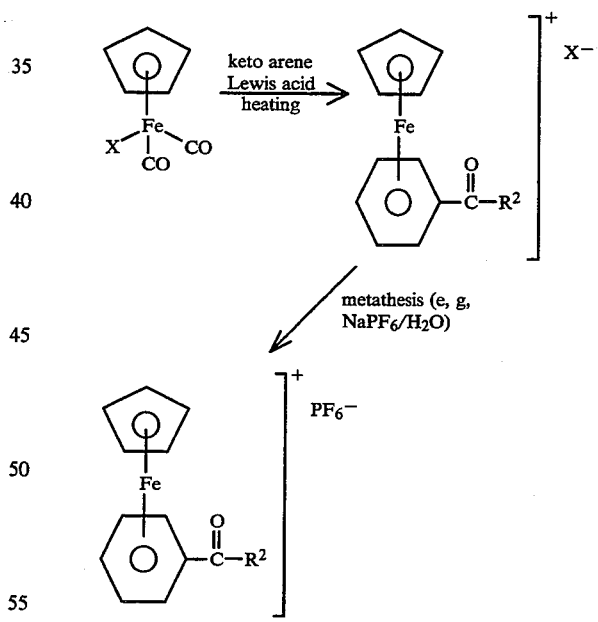

A dicarbonyl-($\eta^5$-cyclopentadienyl)iron(II) halide is reacted with an acyl-alkyl-benzene represented by the formula (2):

$$R^2COC_6H_{5-m}R^1_m \quad (2)$$

wherein $R^1$, $R^2$ and m are as defined above, to produce a (keto-arene)-(cyclopentadienyl) iron halide complex represented by the formula (3):

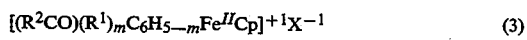

$$[(R^2CO)(R^1)_mC_6H_{5-m}Fe^{II}Cp]^{+1}X^{-1} \quad (3)$$

wherein $R^1$, $R^2$, m, Cp and X are as defined above, in the presence of a Lewis acid at elevated temperatures.

In the alkyl-alkanoyl-benzene or alkyl-benzoyl-benzene of the formula (2) to be substituted for the carbonyl ligands, $R^1$ is an alkyl group having 1 to 5 carbon atoms, preferably 1 to 3. The number of alkyl substituents $R^1$ is from 1 to 5, preferably 3 to 5. In the acyl group $R^2CO$, $R^2$ is a phenyl group or an alkyl group, preferably phenyl group or an alkyl group having 1 to 5 carbon atoms.

Representative examples of the compound (2) are pentamethylacetophenone and pentamethylbenzophenone.

The reaction is usually carried out by dissolving the dicarbonyl-η-cyclopentadienyliron(II) halide in a suitable solvent and heating the solution in the presence of a Lewis acid and the keto arene (2) to be substituted, with stirring. Lewis acids such as aluminum chloride and zinc chloride can be used in the present invention. The Lewis acid is used in an amount of 0.01 to 30% by mole based on the dicarbonyl-$η^5$-cyclopentadienyliron-(II) halide. Suitable solvents are saturated aliphatic types such as hexane, cyclohexane, methylcyclohexane, heptane, isooctane, decahydronaphthalene, and other saturated hydrocarbons. The reaction is usually carried out at a temperature of 90° to 120° C., preferably 100° to 110° C., for 1 to 10 hours. The reaction is carried out preferably in an inert gas.

The produced (keto-arene)-(cyclopentadienyl)iron halide complex (3) is metathesized with an alkali metal salt of a non-nucleophilic acid to give the objective complex salt (1). The metathesis is carried out in a usual manner, for instance, by pouring the reaction mixture obtained in the first step to a large quantity of water for aqueous quench and adding thereto an alkali metal salt of a non-nucleophilic acid such as $NaPF_6$ or an aqueous solution thereof.

The cyclopentadienyliron complex salt (1) of the present invention is useful as a photoinitiator for cationically polymerizable monomers, particularly for epoxy resins. The compound (1) has an absorptivity comparable with or superior to commercially available initiators of the type arene-Fe(II)-Cp. The compound (1) serves as a self sensitized initiator, although it can of course be used in combination with a sensitizer and/or a peroxide.

The best self sensitized initiator complex of the type arene-Fe(II)-Cp currently available is that of naphthalene-Fe(II)-Cp. A plot of molar extinction coefficient vs. wavelength of this material and pentamethylacetophenone-Fe(II)-Cp according to the present invention is shown in FIG. 1. As can be seen, the extinction coefficient at 365 nm for the naphthalene complex is roughly 1000 $M^{-1}cm^{-1}$ while that for the keto arene complex of the invention is approximately 600 $M^{-1}cm^{-1}$. The keto arene complex of the invention shows a significant molar absorptivity extending out to the visible region (>400 nm).

The absorptivity of the keto arene complex of the invention represents a significant improvement over commercially available initiators, such as cumene-Fe(II)-Cp, developed and available through Ciba-Geigy. A typical example of molar absorptivity of these known complexes, namely molar absorptivity of benzene-Fe(II)-Cp, is also shown in FIG. 1. The Ciba-Geigy process disclosed in European Patent 126,712 uses a cumene-Fe(II)-Cp initiator in the presence of a peroxide and an external sensitizer. The sensitizer acts to transfer the long wavelength UV energy to the low lying triplet states of the complex. Once the triplet state is achieved by the complex through this transfer the metal arene π bonds are weakened and the arene slips to the side somewhat allowing the filling of the now empty ligand field of the iron by an epoxy moiety(s). Since the sensitizer must be in contact with the initiator while in its excited state and since the sensitizer is external to the initiator, the efficiency of the process is impaired. The initiator according to the present invention could be considered as "self sensitized" and no migration of sensitizer would be necessary. It would be apparent that the initiator according to the present invention has advantages over the known unsensitized initiator.

Examples of the cationically polymerizable compound to which the photoinitiators according to the present invention are applicable are, for instance, an ethylenically unsaturated compound polymerizable by cationic polymerization mechanism, e.g. a mono- and diolefin such as isobutylene, butadiene, isobutene, styrene, divinylbenzene or N-vinylpyrrolidone, a vinyl ether such as an alkyl vinyl ether or a cyclic vinyl ether, and a vinyl ester such as vinyl acetate; a heterocyclic compound, e.g. an alkylene oxide such as ethylene oxide or propylene oxide, a glycidyl ether of monohydric alcohol or phenol such as n-butyl glycidyl ether or phenyl glycidyl ether, glycidyl acrylate or methacrylate, and a lactone; and other various cationically polymerizable compounds. Examples of the radically polymerizable compound are, for instance, a vinyl compound such as styrene, vinylpyridine, vinyl acetate, divinylbenzene, a vinyl ether, acrylamide, methacrylamide, or an alkyl acrylate or methacrylate; a vinylidene compound such as vinylidene chloride; and the like.

The amount of the initiator according to the present invention is from 0.1 to 15 parts by weight per 100 parts by weight of a polymerizable compound.

The initiator according to the present invention may be used in combination with a known sensitizer such as an aromatic amine, a benzoin alkyl ether or an acetophenone compound, or with an oxidizing agent such as a peroxide.

Since the acylbenzene released by irradiation of ultraviolet rays to the photoinitiator according to the present invention is less toxic than conventional anthracene or pyrene type arene complex salts, and since the benzophenone released by the irradiation acts to initiate a radical polymerization, the photoinitiator according to the present invention has the advantage of an increased environmental salty or a minimized release of an arene into the environment during and after polymerization and curing. It has another advantage of having an ability to initiate a polymerization with almost as small exposure energy as a known anthracene-pentadienyliron(II) salt initiator.

The cyclopentadienyliron complex according to the present invention is also useful as an intermediate for producing an epoxidized arene sandwich complex. The epoxidized arene sandwich complex may be produced, for instance, by directly converting the ketone of the complex to an epoxide via a sulfur ylide, or by maintaining the ketone functionality while attaching an epoxy group to some other position on the arene.

It has also been found that an arene-Fe(II)-Cp can be produced from dicarbonyl-$η^5$-(2,4-cyclopentadien-1-yl)iron(II) halide by a uncatalyzed ligand exchange reaction. In more detail, the present inventors have produced toluene-Fe(II)-Cp $PF_6$ salt in 7.4% by refluxing dicarbonyl-η5-(2,4-cyclopentadien-1-yl)iron(II) iodide in toluene in the absence of a Lewis acid for 15 hours followed by metathesis with NaPF6. The addition of ZnCl2 as a Lewis acid to the above reaction system increases the yield to 11%. This fact indicates that it would be possible to produce complexes of the Cp-Fe(II)-arene without using a Lewis acid. This method is advantageous for producing complexes containing arenes which are not otherwise possible due to their incompatibility with the Lewis acid conditions.

The present invention is more specifically described and explained by means of the following Examples, in which all parts and parcentages are by weight unless otherwise noted.

EXAMPLES 1 AND 2

All the operations were effected in dry nitrogen and in the dark room.

In 100 ml of methylcyclohexane was dissolved 1 g of dicarbonyl-η5-(2,4-cyclopentadien-1-yl)iron(II) chloride. To the resulting solution were added the keto-arene shown in Table 1 and a fivefold excess of aluminum chloride. The mixture was heated at a temperature of 100° to 110° C. for one half hour with stirring, and was then poured into a large quantity of water (50 ml). Thereto was added an excess NaPF6 solution (2.5 g in 10 ml water) to give a mixture of PF6 salts. The separation of the salts was effected by column chromatography and recrystallization from CH2Cl2 and ethyl ether.

Figure 2:
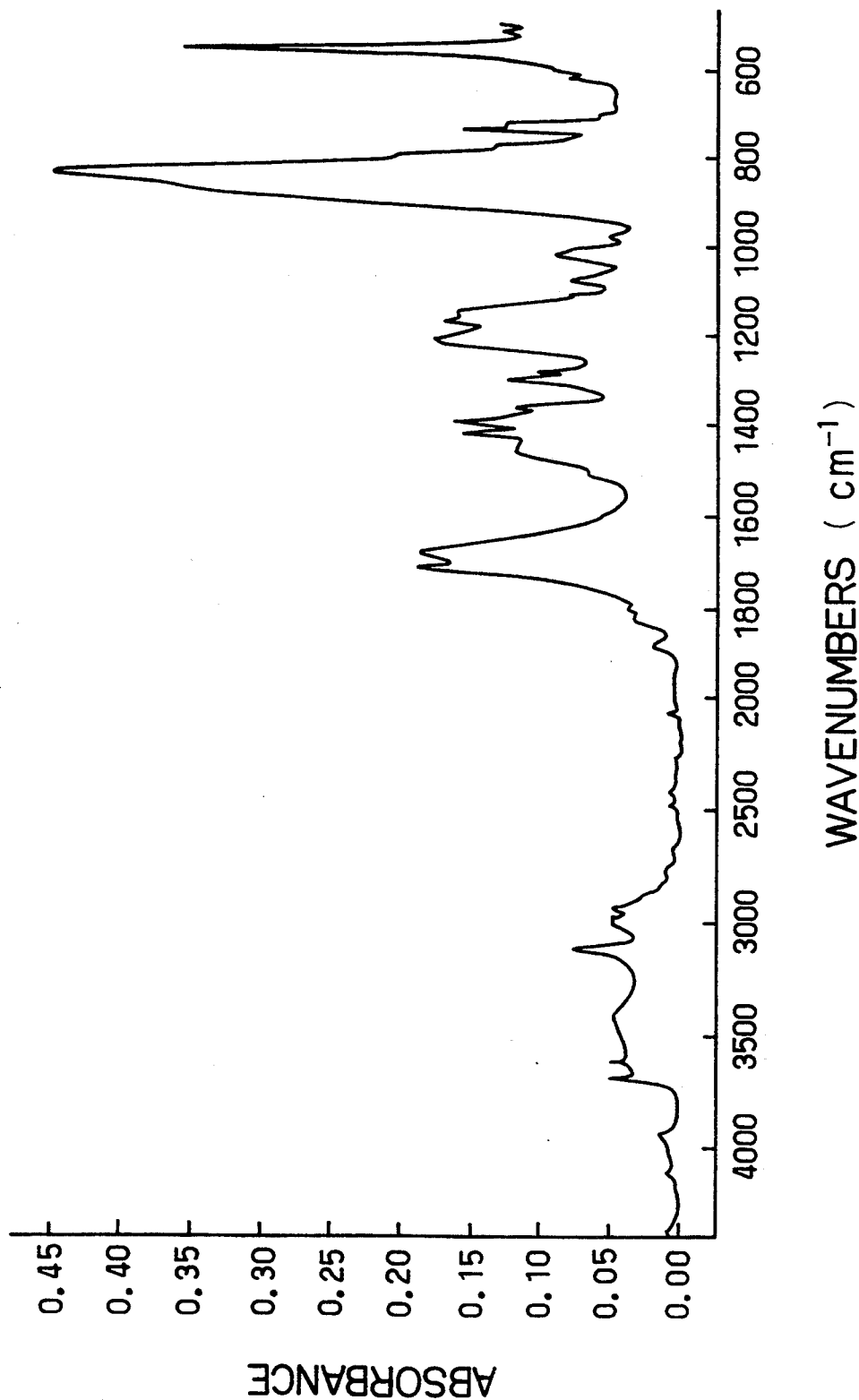
FIG. 2 is a FTIR spectrum of (acetylpentamethyl-$\eta^6$-benzene)-($\eta^5$-cyclopentadienyl)iron(II) hexafluorophosphate.
Figure 3:
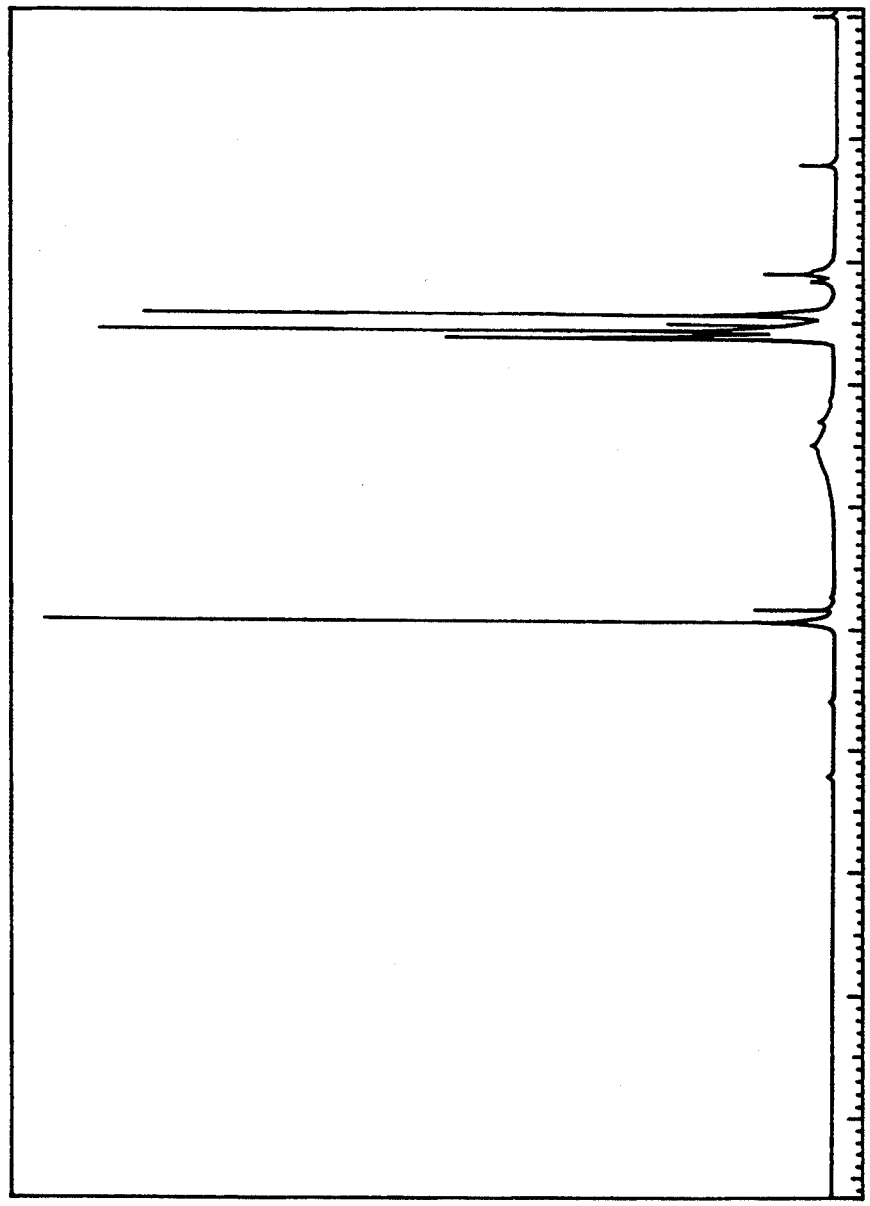
FIG. 3 is a $^1$H-NMR spectrum of (acetylpentamethyl-$\eta^6$-benzene)-($\eta^5$-cyclopentadienyl)iron(II) hexafluorophosphate.
Figure 4:
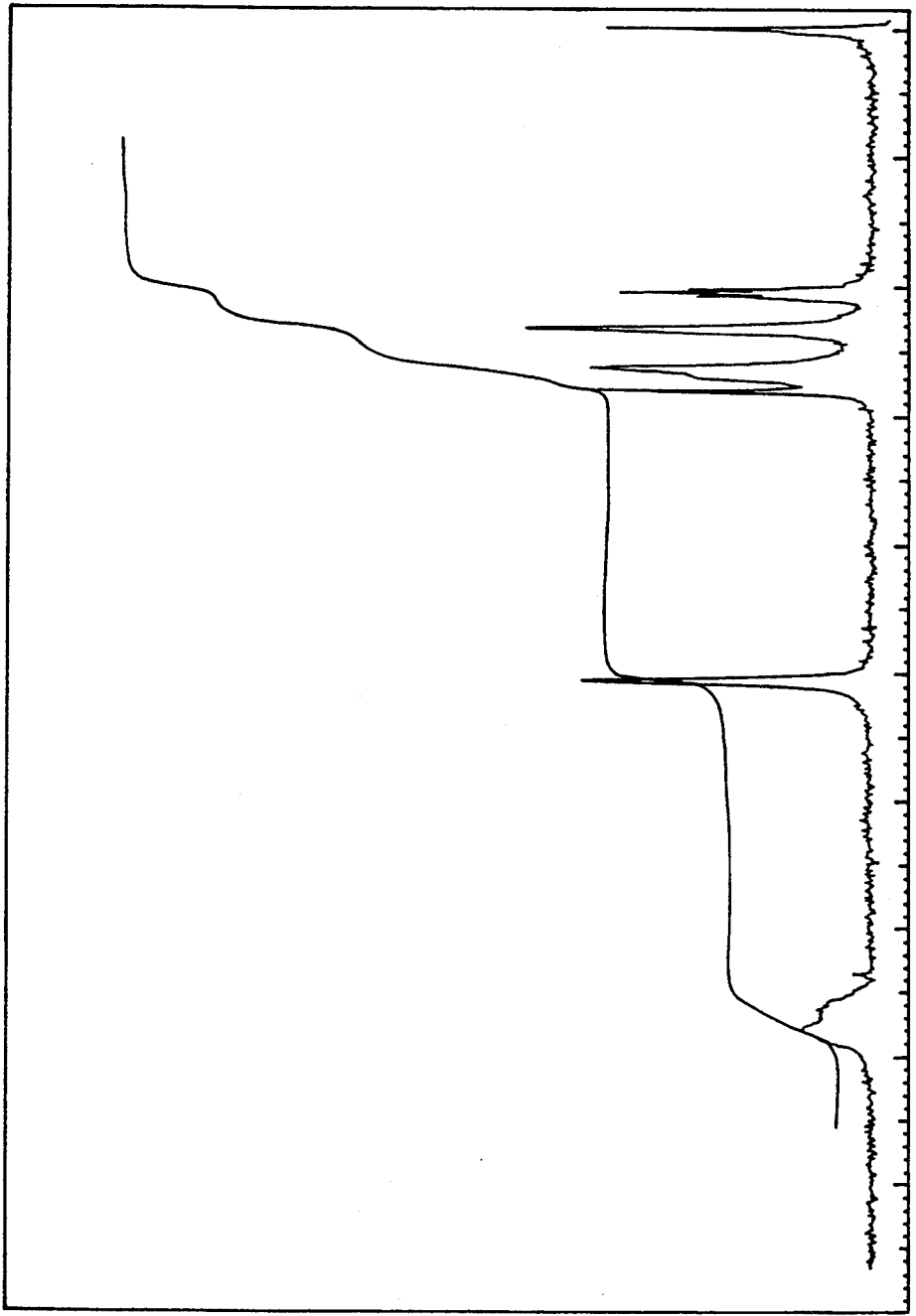
FIG. 4 is a $^1$H-NMR spectrum of (benzoylpentamethyl-$\eta^6$-benzene)-($\eta^5$-cyclopentadienyl)iron(II) hexafluorophosphate.

The product and the yield are shown in Table 1. Determination of the products was made by NMR and IR analyses. The 1H-NMR and FTIR spectra of the obtained (acetyl-pentamethyl-η6-benzene)-(η5-cyclopentadienyl)iron(II) hexafluorophosphate are shown in FIGS. 2 and 3. The 1H-NMR spectrum of the obtained (benzoyl-pentamethyl-η6-benzene)-(η5-cyclopentadienyl)iron(II) hexafluorophosphate is also shown in FIG. 4.

TABLE 1

| Ex. No. | Keto-arene Compound | Amount (equivalents) | End product Yield | End product Compound |
|---|---|---|---|---|
| 1 | Pentamethyl-acetophenon | 5 | 16.6% | *1 |
| 2 | Pentamethyl-benzophenon | 2 | 3.9% | *2 |

(Notes)
*1: (acetyl-pentamethyl-η6-benzene)-(η5-cyclo-pentadienyl)iron(II) hexafluorophosphate
*2: (benzoyl-pentamethyl-η6-benzene)-(η5-cyclo-pentadienyl)iron(II) hexafluorophosphate

EXAMPLES 3 TO 6 AND COMPARATIVE EXAMPLES 1 TO 4

Using cyclopentadienyliron(II) complex salts produced in Examples 1 and 2 and a known cyclopentadienyliron(II) complex salt as photoinitiators, an epoxy resin or a mixture thereof with an acrylic monomer was cured in the manner described below.

In each Example or Comparative Example, the monomer or monomers and a photoinitiator were mixed in the amounts shown in Table 2 in the dark room. The mixture was uniformly applied on a glass plate with a bar coater. The coated film was exposed with a 80 W/cm mercury lamp for the period shown in Table 2, followed by heating at 80° C. for 5 minutes. The exposure period required for the curing was determined by measuring the time until the coated film became free of tack to touch.

TABLE 2

| Example or Comparative Example No. | Example | | | | Comparative Ex. | | | |
|---|---|---|---|---|---|---|---|---|
| | 3 | 4 | 5 | 6 | 1 | 2 | 3 | 4 |
| Epoxide | 100 | 100 | 50 | 50 | 100 | 50 | 100 | 50 |
| Monomer (A)*3 (part) | | | | | | | | |
| Acrylic Monomer (B)*4 (part) | | | 50 | 50 | | 50 | | 50 |
| Photoinitiator (I)*5 (part) | 5 | 5 | | | | | | |
| Photoinitiator (II)*6 (part) | | | 5 | 5 | | | | |
| Photoinitiator (III)*7 (part) | | | | | 5 | 5 | | |
| Exposure period required for curing | 35 | 30 | 25 | 20 | 40 | 80 | >100 | >100 |
| | | | | | | | *8 | *8 |

TABLE 2-continued

| Example or Comparative Example No. | Example | | | | Comparative Ex. | | | |
|---|---|---|---|---|---|---|---|---|
| | 3 | 4 | 5 | 6 | 1 | 2 | 3 | 4 |
| (second) | | | | | | | | |

(Notes)

*3: Epoxide monomer (A) 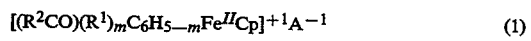

*4: Acrylic monomer (B)

*5: Photoinitiator(I)

*6: Photoinitiator(II) 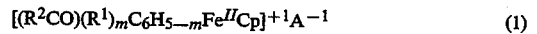

*7: Photoinitiator(III)

*8 The compositions of Comparative Examples 3 and 4 were not cured.

In addition to the ingredients used in the Examples, other ingredients can be used in the Examples as set forth in the specification to obtain substantially the same results.

What is claimed is:

1. A cyclopentadienyliron complex salt represented by the formula (1):

$$[(R^2CO)(R^1)_mC_6H_{5-m}Fe^{II}Cp]^{+1}A^{-1} \quad (1)$$

wherein $R^1$ is a methyl group, m is an integer of 5, $R^2$ is a methyl group or phenyl group, Cp is an $\eta^5$-cyclopentadienyl group and $A^{-1}$ is a non-nucleophilic anion selected from the group consisting of $BF_4^-$, $PF_6^-$, $AsF_6^-$, $SbF_6^-$ $FeCl_4^-$, $SnCl_5^-$, $SbCl_6^-$ and $BiCl_5^-$.

2. The complex salt of claim 1 which is (acetyl-pentamethyl-$\eta^6$-benzene)-($\eta^5$-cyclopentadienyl)iron(II) hexafluorophosphate.

3. The complex salt of claim 1 which is (benzoyl-pentamethyl-$\eta^6$-benzene)-($\eta^5$-cyclopentadienyl)iron(II) hexafluorophosphate.

4. A photopolymerizable composition comprising:
   (a) at least one polymerizable compound selected from the group consisting of a radically polymerizable compound and a cationically polymerization compound, and
   (b) a cyclopentadienyliron complex salt represented by the formula (1):

$$[(R^2CO)(R^1)_mC_6H_{5-m}Fe^{II}Cp]^{+1}A^{-1} \quad (1)$$

wherein $R^1$ is a methyl group, m is an integer of 5, $R^2$ is a methyl group or phenyl group, Cp is an $\eta^5$-cyclopentadienyl group and $A^{-1}$ is a non-nucleophilic anion selected from the group consisting of $BF_4^-$, $PF_6^-$, $AsF_6^-$, $SbF_6^-$, $FeCl_4^-$, $SnCl_5^-$, $SbCl_6^-$ and $BiCl_5^-$.

5. The photopolymerizable composition of claim 4, wherein the complex salt is (acetyl-pentamethyl-$\eta^6$-benzene)-($\eta^5$-cyclopentadienyl)iron(II) hexafluorophosphate.

6. The photopolymerizable composition of claim 4, wherein the complex salt is (benzoyl-pentamethyl-$\eta^6$-benzene)-($\eta^7$-cyclopentadienyl)iron(II) hexafluorophosphate.

* * * * *